United States Patent [19]

Onwumere et al.

[11] Patent Number: 5,250,649

[45] Date of Patent: * Oct. 5, 1993

[54] MELT PROCESSABLE POLYURETHANEUREA COPOLYMERS AND METHOD FOR THEIR PREPARATION

[75] Inventors: Fidelis C. Onwumere, Miamisberg; Donald D. Solomon, Spring Valley, both of Ohio

[73] Assignee: Becton, Dickinson and Company, Franklin Lakes, N.J.

[*] Notice: The portion of the term of this patent subsequent to Aug. 14, 2007 has been disclaimed.

[21] Appl. No.: 546,825

[22] Filed: Jun. 29, 1990

[51] Int. Cl.$^5$ .............................................. C08G 18/00
[52] U.S. Cl. ....................................... 528/44; 528/28; 528/54; 528/76; 528/77; 528/83; 528/84
[58] Field of Search ....................... 528/44, 28, 54, 76, 528/77, 83, 84

[56] References Cited

U.S. PATENT DOCUMENTS 4,719,247  1/1988  Un et al. ................................ 521/159
4,948,860  8/1990  Solomon et al. ....................... 528/28

OTHER PUBLICATIONS

Phillips et al., *The Use of Segmented Polyurethane in Ventricular Assist Devices and Artificial Hearts,* Synthetic Biomedical Polymers, M. Szycher and W. J. Robinson ed. Technomic Publishing Co., Inc. Westport, Ct. 1980, p. 39.

*Primary Examiner*—John Kight, III
*Assistant Examiner*—Duc Truong
*Attorney, Agent, or Firm*—Richard E. Brown

[57] ABSTRACT

Melt processable polyurethaneureas are prepared from a diisocyanate, a polyglycol, a diol chain extender and an amine terminated polyether. Water may be included as a reactant, and the polymer may contain an additive such as a radiopaque material and a coating of an antithrombogenic agent or an antimicrobial agent. The invention includes a one-pot bulk polymerization method for preparation of the polymers.

23 Claims, No Drawings

MELT PROCESSABLE POLYURETHANEUREA COPOLYMERS AND METHOD FOR THEIR PREPARATION

BACKGROUND OF THE INVENTION

1. Field of the Invention

This invention relates to copolymers, and more specifically relates to melt processable polyurethaneureas and to a method for their preparation.

2. Background of the Invention

Polyurethane block copolymers possess an outstanding balance of physical and mechanical properties and superior blood compatibility compared to other polymers such as silicone rubber, polyethylene, polyvinyl chloride and perfluorinated polymers. As a result, they have come to the fore as the preferred polymeric biomaterials for fabrication of various medical device components. Some important device applications for polyurethanes include peripheral and central venous catheters, coatings for heart pacemaker leads and the Jarvik heart.

Polyurethanes are synthesized from three basic components, a polyisocyanate, a polyglycol and an extender, usually a low molecular weight diol, diamine, aminoalcohol or water. If the extender is a diol, the polyurethane consists entirely of urethane linkages. If the extender is water, aminoalcohol or a diamine, both urethane and urea linkages are present and the polyurethane is more accurately and conventionally termed a polyurethaneurea. In this disclosure, polyurethaneurea will hereinafter be abbreviated as PUU.

The usual polyglycols are polyethylene glycol (PEG) and polytetramethylene ether glycol (PTMEG). Polypropylene ether glycol (PPG), while providing a polyurethane of desirable high softness, is infrequently used for polyurethanes intended for medical use because PPG requires a catalyst for reaction with isocyanates. The usual catalysts for polyurethane synthesis, such as dibutyl tin dilaurate, are toxic and contraindicated for medical grade polyurethane synthesis because of the danger of leaching into a patient's body fluid.

Polyurethanes and PUU develop microdomains conventionally termed hard segments and soft segments, and as a result are often referred to as segmented polyurethanes. The hard segments form by localization of the portions of the polymer molecules which include the isocyanate and extender components and are generally of high crystallinity. The soft segments form from the polyether glycol portions of the polymer chains and generally are either noncrystalline or of low crystallinity. Crystallinity and hard segment content are factors which contribute to melt processability.

It is known that PEG is clear viscous liquid at molecular weights below about 900 and is an opaque white solid of increasing hardness as the molecular weight increases above 900. PPG is essentially noncrystalline regardless of its molecular weight whereas PTMEG develops some crystallinity at higher molecular weight. With PTMEG, the normal chain mobility of the soft segment is decreased as the level of crystallinity increases due to the infusion of crystallites of the soft segment into the hard segment. This in turn affects the elastomeric character of the polymer. Nevertheless, polyurethanes made from PTMEG are generally melt processable, but catheters extruded therefrom are less flexible than catheters fabricated from PEG and PPG.

PPG, being totally noncrystalline, gives a polyurethane having maximum phase separation between the hard and soft segments. As a result, PPG derived polyurethanes are soft and elastomeric, and the softness is affected by small changes in temperature. Thus, at body temperature, a typical PPG polymer is about 75 to 90% softer than at room temperature as compared to a 60 to 75% change shown by a typical PTMEG derived polyurethane.

As is well-known in the art, PUU made with diamine extenders are generally not melt processable regardless of the polyglycol used as the soft segment. For example, a PUU well-known as an industrial fiber (Lycra ® DuPont de Nemours and Co.) has been extensively studied under the trade name Biomer ® (Ethicon Corp.) for fabrication of various biomedical devices. A review of these studies and the many salubrious properties of PUU has been presented by Phillips et al., *The Use of Segmented Polyurethane In Ventricular Assist Devices and Artificial Hearts*, in Synthetic Biomedical Polymers, M. Szycher and W. J. Robinson, ed. Technomic Publishing Co., Inc., Westport, Conn., 1980, page 39. However, as stated by Phillips et al., Biomer ® presents some fabrication difficulties that limit production techniques. Biomer ® has a melt temperature higher than the decomposition temperature of the urethane functionality and therefore can be spun or cast only from solution, i.e., it cannot be melt extruded or injection molded. Severe limitations are thereby imposed on its fabrication latitude. Further, it is essentially insoluble in all solvents except DMAC which of course must be completely removed if the product is to be used in a biomedical article.

Since PUUs, such as Biomer ® are well known to be highly biocompatible, a PUU which would combine the biocompatibility of Biomer ® with the melt processability of polyurethanes would be a desirable product. One approach to this objective is disclosed in copending application serial number 345,800, filed on May 1989, of common assignee with the present invention. This application discloses a melt processable PUU having both a diol and diamine chain extender. The instant application discloses another class of melt processable PUU.

SUMMARY OF THE INVENTION

One aspect of the present invention is a melt processing PUU prepared by reaction of a polyisocyanate, a polyglycol, a chain extending diol and an amine terminated soft segment component, preferably an amine terminated polyether. Preferred PUUs are prepared from a diisocyanate such as 4,4'-diphenylmethane diisocyanate (MDI) and a polyether glycol, such as PEG or PTMEG. The polyglycol component may include a silicone glycol. Preferred diol extenders are ethylene glycol and 1,4-butanediol (BDO). The preferred amine terminated polyether is amine terminated polypropylene oxide. Water may be included in the reaction mixture and, in the form of moist air, may also serve to cure the polymer. The polymer may include various additives, such as a radiopaque agent.

Another aspect of the invention is a catalyst free method to prepare the PUU of the invention. The preferred method is a one-pot reaction in which all the components are combined with efficient stirring. An exotherm takes place during the polymerization reaction, after which the polymer may be transferred to a tray for spontaneous moisture cure at an appropriate temperature.

Thus, the invention provides a PUU particularly useful for catheter fabrication, most particularly for fabrication of blood contacting catheters. The PUU of the invention provides a combination of advantages seen only individually with prior art catheters. Thus, the catheter of the invention is stiff for insertion into a patient's blood stream, as are prior art catheters formed from polymers such as polyvinyl chloride or polytetrafluoroethylene. However, in contrast to catheters made of these polymers, the initially stiff PUU catheter of the invention softens after insertion for patient comfort and minimization of mechanically induced phlebitis during movement of the catheter.

Prior art polyurethane catheters having polyethylene oxide soft segments do soften, but these catheters do not provide the stiffness necessary for insertion. Further, most soft polyurethane catheters of the prior art require a catalyst for the reaction of the polyol and diisocyanate. Conventional catalysts are toxic and may leach out of a catheter in contact with a body fluid. The PUU of the invention provides softness resulting from the polyol and is made without a catalyst due to the reactivity of the amino terminal groups.

Prior art PUU catheters, such as those made of Biomer ® provide a high level of hemocompatibility. Biomer ® however, cannot be melt processed so that Biomer ® catheters can only be made by solution extrusion. The PUU of the invention, on the other hand, provides hemocompatibility in a melt extruded catheter. By avoiding solution extrusion, processing is greatly simplified and the problem of completely removing toxic solvents such as dimethylacetamide is not encountered.

In addition to having advantages accruing from conventional melt processing techniques, the PUUs of the invention may be developed and expanded into a broad new class of polymeric biomaterials and devices through polymer alloys, chemical modification, grafting, surface coating treatments and co extrusion. Such material should potentially provide a novel range of physical/mechanical properties, enhanced blood and tissue compatibility as well as selective moisture vapor, gas transmission and controlled release characteristics.

DETAILED DESCRIPTION

While this invention is satisfied by embodiments in many different forms, there will herein be described in detail preferred embodiments of the invention with the understanding that the present disclosure is to be considered as exemplary of the principles of the invention and is not intended to limit the invention to the embodiments described. The scope of the invention will be measured by the appended claims and their equivalents.

The novel polymers of the invention may be used in a number of applications requiring soft, elastomeric, blood compatible, and tissue compatible polymers. For example, they have excellent applicability in virtually all central venous access catheter products, urinary catheters, vascular grafts, and long term implantable catheters, which require stiffness for insertion but softness for patient comfort and safety during advancement through a tortuous blood vessel. They may also be useful for products such as hemodialysis catheters, introducer catheters, obturators and peripheral catheters.

In accordance with the present invention, a melt processable PUU having a desirable balance between stiffness and softness is obtained by combining two or more components in the soft segment. One component is a polyglycol, i.e., a polymer having terminal hydroxyl groups. Another component is an amine terminated polyether. The PUU of the invention also includes a conventional polyisocyanate and chain extender.

Polyisocyanates useful in the present invention may have two or more isocyanate groups. Preferred polyisocyanates are aromatic or alicyclic diisocyanates, such as MDI, toluene diisocyanate, isophorone diisocyanate, methylene bis (4-cyclohexyl isocyanate), hexamethylene diisocyanate and the like. Of these, MDI is preferred.

The chain extender component may be water or a low molecular weight branched or unbranched diol, diamine or amino alcohol. Preferred extenders are diols. Representative nonlimiting examples of chain extenders are ethylene glycol, diethylene glycol; triethylene glycol; 1,2-propanediol; 1,3-propanediol; 1,6-hexanediol; 1,4-bis-hydroxymethyl cyclohexane, hydroquinone dihydroxyethyl ether, ethylenediamine, hexamethylenediamine and ethanolamine. The preferred extender is BDO.

The polyglycol component of the soft segment may be a polyester glycol, a polysiloxane glycol, a polyether glycol or a polythioether qlycol. The polyglycol component may have a molecular weight of about 500 to 16,000 and preferably is a polyether. The most preferred polyglycol is PTMEG having a molecular weight of about 400 to 4,000, preferably about 500 to 3,000, most preferably about 650 to 1,000. These products are available commercially under the trade names Polymeg ® (Quaker Oats Co., Chemical Division) and Terathane ® (DuPont), respectively.

The amine terminated component of the soft segment may be an amine terminated polymer which includes ester and urea linkages in the polymer chain. Alternatively, an amine terminated polysiloxane may be included. These products, such as aminopropyldimethyl and aminoobutyldimethyl terminated polysiloxane are available commercially from Petrarch Systems, Bristol, Penna.

Preferred amine terminated soft segment components are polyethers commercially available under the trade name Jeffamine ® from Texaco Chemical Co. (Bellair, Tex.). These products are hereinafter designated as JA. The JA may include repeating units of polyethylene oxide, polypropylene oxide or polytetramethylene oxide and may have a molecular weight of about 400 to 8,000. Preferred JAs have polypropylene oxide repeating units. The most preferred JA is an amino terminated polypropylene oxide having a molecular weight of about 4,000 sold under the trade name Jeffamine ® D 4000.

The ratio of the polyglycol and amine terminated components of the soft segment may be about 10:1 to 1:10, preferably about 4:1 to 1:1, most preferably about 2:1 to 1:1. (All percentages and ratios in this disclosure are by weight unless otherwise specified.)

It is believed, although not substantiated, that the stiffness of the preferred PUU of the invention comes from the hard segment and the softness after insertion into the body is the result of the tetramethylene oxide and propylene oxide repeating units.

The diisocyanate and chain extender make up the hard segment of the PUU composition. Compositions which may be prepared by the method of the invention may have hard segments of about 25 to 70%, preferably about 35 to 55%.

The ratio of the ingredients which may be used is based on the reaction of one isocyanate group with one alcohol or amino group from the polyglycol, JA or extender. Thus, the ratio of the total isocyanate groups in the diisocyanate to the total hydroxyl and amino groups present is conventionally referred to as the isocyanate index (II) and may be from about 1.00 to 1.30 preferably from about 1.00 to 1.05, most preferably about 1.02. The quantities of the ingredients to be mixed may be calculated from the predetermined ratio of desired hard and soft segments and the known equivalent weights of the diisocyanate, polyglycol, JA and extender Excess isocyanate groups present in formulations of high II may be reacted with water during the curing step, as described below.

It will be appreciated by one skilled in the art that blocks of both the polyglycol and JA are present in the PUU of the invention. Thus, for example, the PUU may have as a representative structure

- MDI - PTMEG - MDI - JA - MDI - BDO - MDI with the understanding that the hyphens represent covalent bonds formed between the indicated reaction components and that the terminal isocyanate groups are hydrolyzed by the chain extender in the formulation, or preferably during a moisture cure, to amino groups which may react with other isocyanate groups to give blocks of additional hard segment.

Synthesis of the polymer of the invention may be carried out by the conventional two step or prepolymer method or preferably by the one shot or bulk method. In the prepolymer method, the soft segment components are reacted with the diisocyanate to give a prepolymer having terminal isocyanate groups. The isocyanate-terminated prepolymer may then be reacted with the chain extender.

In one preferred bulk polymerization process of the invention, conventional polymerization equipment is charged with the extender, polyglycol and JA in proportions predetermined in accordance with the desired hard segment soft segment ratio. With vigorous stirring, the diisocyanate may be added all at once. If the reaction does not start spontaneously, the mixture may be heated sufficiently to induce an exothermic reaction. The reaction mixture may be stirred vigorously until the exotherm is complete and the temperature begins to drop off, generally for about 1 to 5 minutes. The clear homogeneous melt, while still hot, may advantageously be removed from the reactor prior to curing.

In an alternative procedure, the polyglycol JA and diisocyanate may be mixed with stirring, and, when the initial exotherm begins to subside, the extender may be added with continued stirring.

The reaction may be carried out for about 1 second to 10 minutes, preferably about 15 seconds to 5 minutes, most preferably for about 1 to 2 minutes. In general, the exotherm reaches about 100° C. before subsiding.

Any conventional method may be used to effect curing. Preferably, the melt is simply set aside for a suitable time and temperature, as, for example, from ambient to about 125° C. and for about 1 hour to 20 days, to be cured by atmospheric moisture.

Any polymerization equipment or technique which provides a clear melt at the conclusion of the exotherm may be used. Preferred equipment includes a multi-paddle shaft driven at high rotation rate by a motor. Exemplary of such a system is the Fluidyne Model 63014 Microshot Elastomer Processing System.

The above described procedures for synthesis of the PUU of the invention do not include a catalyst. In contrast, prior art polyurethanes having PPG soft segments require a catalyst because of the low reactivity of PPG due to its secondary alcohol group. The polymers of the invention have the advantages provided by polypropylene oxide soft segments but overcome the requirement of the catalyst because of the reactivity of the terminal amino groups.

The polyurethane resins of the invention may be fabricated into an article of any desired shape such as film, tubing and other forms by conventional thermoplastic fabricating techniques including melt casting, extrusion molding, etc. The resin may have incorporated therein, as desired, conventional stabilizers, radiopaque materials such as barium sulfate, and the like. The radiopaque agent may be included as coextruded stripes, as is well known in the catheter art. The amounts of these materials will vary depending upon the application of the polyurethane, but they are typically present in amounts ranging from about 25 to 40 weight percent of the polymer.

The shaped article may also include an antithrombogenic agent and/or an antimicrobial agent either bulk distributed into the polymer prior to melt processing or coated onto the article after fabrication. Representative nonlimiting agents such as heparin, chlorhexidene and penicillin may be used. A suitable coating procedure is, for example, application of a coating of a quaternary ammonium salt to the article surface and reaction of the salt with the agent. Bulk distribution and coating procedures for antithrombogenic and antimicrobial agents are well known in the art and no further details with respect to this aspect of the invention are needed for a full understanding of the invention by one skilled in the art.

Tensile strength is a measure of the force, generally given in pounds per square inch (psi) required to break a polymer. Elongation is a measure of the ability of a polymer to stretch without breaking, and is generally reported as a percentage of an initial value. The term modulus defines the force, in psi, required to stretch a polymer to a given percentage of elongation.

The tensile, elongation and modulus of the PUU of the invention may be measured by ASTM procedure D638 using an Instron Universal Testing Instrument, Model 1122. The physical properties of a representative polymer of the invention is given in the Chart which accompanies Example V below.

The following Examples are provided to further describe the invention but are not to be considered in any way to be limitative of the invention.

EXAMPLE 1

Synthesis of a Representative PUU Having a Hard Segment of 60% and II of 1.02

To a half gallon tin can was added 320 g of PTMEG (1000 mwt), 160 of Jeffamine ® D4000 and 164 of 1,4-butane diol. With rapid high shear stirring, the components were mixed thoroughly. After mixing, and with continuous stirring, 556 g of MDI was added all at once and an exotherm of about 100° C. was reached within 1 minute. The clear viscous melt was immediately poured into a tray and cured in an oven at 125° C. for 1 hour.

EXAMPLE II

In the same way as described in Example I, other PUU of the invention having hard segment contents of 50,45,40 and 35 and a 2:1 ratio of PTMEG and JA were made by appropriate changes in the component ratios.

EXAMPLE III

In the same way as described in Example I, a PUU was prepared using only Jeffamine ® D4000 as the soft segment. This polymer was not melt processable.

EXAMPLE IV

Thermal Extrusion of PUU of Examples I and II

The PUUs were extruded into a tube with a 1 inch diameter barrel extruder using the following extrusion conditions:

| TEMPERATURE (°F.) | |
|---|---|
| Zone 1 | 360 |
| Zone 2 | 390 |
| Zone 3 | 410 |
| Zone 4 | 410 |
| Zone 5 | 410 |
| Zone 6 | 410 |
| Pump Melt | 402 |
| Screw RPM | 24 |
| Screw AMPS | 4.4 |
| Pump Inlet Pressure | 1000 PSI |
| Pump Outlet Pressure | 700 |
| Pump AMPS | 1.4 |

EXAMPLE V

Bend Force Measurement of Stiffness

The bend force is the axial force (in grams) required to bend a two inch length of catheter tubing using an Instron machine, model 1122. The PUUs of the invention were extruded by the procedure of Example IV into a 7 French trilumen cather tubing. Sections of the tubing 2 inches long were conditioned 40 hours at 23° C. and relative humidity of 50%. Bend forces were determined in normal saline solution after 1 hour at 37° C.

| Sample | Hard Segment | Bend Force, gr | | Percent Softening | Physical Properties | | | | | |
|---|---|---|---|---|---|---|---|---|---|---|
| | | Initial | 1 hour | | Tensile lbs. | Modulus, % | | | | Elongation Percent |
| | | | | | | 5 | 25 | 50 | 100 | |
| PU* | 50 | 230 ± 10 | 89 ± 4.5 | 61 | 25.7 | 2.5 | 5.7 | 6.3 | 6.8 | 463 |
| PUU | 60 | 1748 ± 191 | 170 ± 43 | 90 | | | | | | |
| PUU | 50 | 834 ± 34 | 95 ± 4 | 89 | 19.0 | 4.1 | 6.6 | 7.3 | 7.9 | 372 |
| PUU | 45 | 250 ± 9 | 57 ± 2 | 77 | | | | | | |
| PUU | 40 | 120 ± 5 | 42 ± 2.5 | 65 | | | | | | |
| PUU | 35 | 88 ± 4 | 33 ± 3 | 63 | | | | | | |

*Vialon ® polytetramethylene ether glycol based polyurethane

EXAMPLE VI

Comparison of Softening Characteristics of PUU, Novolon ®* and Vialon ® Catheters A 24 gauge catheter was extruded from the 60% hard segment PUU of the invention. This catheter and 24 gauge catheters of Vialone ® and Novolon ® were maintained in normal saline solution at 37° C. for 30 minutes. Bend forces were determined for each by the procedure of Example V.

| Sample | Bend Force (gr) | | Percent Softening |
|---|---|---|---|
| | Initial | 30 min. | |
| Novolon ® | 30 ± 5 | 27 ± 4 | 10 |
| PUU | 35 ± 5 | 2.4 ± 0.4 | 93 |
| Vialon ® | 14 ± 1.2 | 3.7 ± 2 | 74 |

*Polytetrafluoroethylene

It is seen from Examples V and VI that the PUU catheter of the invention has a much greater initial stiffness for ease of insertion than the polytetramethylene ether glycol based polyurethane and even has a somewhat greater stiffness than the polytetrafluoroethylene catheter. However, after contact with the saline, the initially stiff PUU softens to the level of the polyurethane, but the polytetrafluoroethylene remains substantially unchanged.

What is claimed is:

1. A melt processable polyurethaneurea consisting essentially of a product reaction of a diisocyanate, a polyetherglycol, a diol chain extender, an amine terminated polyether and atmospheric moisture as a curing agent, said polyurethaneurea having amino end caps as a result of being cured with said atmospheric moisture.

2. The polyurethaneurea of claim 1 wherein said diisocyanate is selected from the group consisting of 4,4'-diphenylmethane diisocyanate, toluene diisocyanate, isophorone diisocyanate, methylene bis (4-cyclohexyl isocyanate), and hexamethylene diisocyanate.

3. The polyurethaneurea of claim 1 wherein said polyetherglycol is selected from the group consisting of polyethyleneglycol and polytetramethylene ether glycol.

4. The polyurethaneurea of claim 1 wherein said diol is selected from the group consisting of 1,4-butanediol, ethylene glycol; diethylene glycol; triethylene glycol; 1,2-propanediol; 1,3-propanediol; 1,6-hexanediol; 1,4-bis-hydroxymethyl cyclohexane, and hydroquinone dihyroxyethyl ether.

5. The polyurethaneurea of claim 1 wherein said amino terminated polyether is selected from the group consisting of amine terminated polyethylene oxide, amine terminated polypropylene oxide and amine terminated polytetramethylene oxide.

6. The polyurethaneurea of claim 1 further including a component selected from the group consisting of a radiopaque material, an antithrombogenic agent, an antimicrobial agent and water.

7. A melt processable polyurethaneurea consisting essentially of a product from the reaction of a polyisocyanate, chain extender, polyglycol, polymeric amine terminated soft segment component selected from the group consisting of an amine terminated polyether, polyester, polyurea and polysiloxane, and atmospheric moisture as a curing agent, said polyurethaneurea having amino end caps as a result of being cured with said atmospheric moisture.

8. The polyurethaneurea of claim 7 wherein said component has a linkage selected from the group consisting of a urea, ester, siloxane and ether linkage in the polymer chain.

9. The polyurethaneurea of claim 7 wherein said chain extender is selected from the group consisting of a diol, diamine, amino alcohol and water.

10. The polyurethaneurea of claim 7 wherein said polyglycol is selected from the group consisting of a polysiloxane lycol, a polyester lycol and a polyether glycol.

11. A melt processable polyurethaneurea consisting essentially of a product from the reaction of 4,4'-diphenylmethane diisocyanate, 1,4-butanediol, polytetramethyleneether glycol, amine terminated polypropylene oxide and atmospheric moisture as a curing agent, said polyurethane having amino end caps as a result of being cured with said atmospheric moisture.

12. The polyurethaneurea of claim 11 further consisting essentially of an agent selected from the group consisting of a radiopaque agent, an antithrombogenic agent and an antimicrobial agent.

13. A method for producing a melt processable polyurethaneurea consisting essentially of combining with mixing a diisocyanate and a mixture of a polyetherglycol, a diol chain extender and an amine terminated polyether at a temperature sufficient to induce an exotherm to give a clear and uniform melt of polyurethaneurea and curing said polyurethaneurea with said atmospheric moisture.

14. The method of claim 13 wherein said combining step is performed with a diisocyanate selected from the group consisting of 4,4'-diphenylmethane diisocyanate, toluene diiso cyanate, isophorone diisocyanate, methylene bis (4-cyclohexyl isocyanate), and hexamethylene diisocyanate.

15. The method of claim 13 wherein said combining step is performed with a polyetherglycol selected from the group consisting of polyethyleneglycol and polytetramethylene ether glycol.

16. The method of claim 13 wherein said combining step is performed with a diol selected from the group consisting of 1,4-butanediol, ethylene glycol; diethylene glycol; triethylene glycol; 1,2-propanediol; 1,3-propanediol; 1,6-hexanediol; 1,4-bis-hydroxymethyl cyclohexane and hydroquinone dihydroxyethyl ether.

17. The method of claim 13 wherein said combining step is performed with an amine terminated polyether selected from the group consisting of polyethylene oxide, polypropylene oxide and polytetramethylene oxide.

18. The method of claim 13 wherein said combining step is performed with a reagent selected from the group consisting of water and a radiopaque material.

19. The method of claim 13 further consisting essentially of extruding said polyurethaneurea into a tubing and coating said tubing with an agent selected from the group consisting of an antithrombogenic agent and an antimicrobial agent.

20. The method of claim 13 further consisting essentially of coextruding said polyurethaneurea into a tubing having a coextruded stripe which includes a radiopaque material.

21. A method for producing a melt processable polyurethaneurea consisting essentially of combining with mixing a polyisocyanate, a polyglycol, a chain extender and an amine terminated polyether at a temperature sufficient to induce an exotherm to give a clear and uniform melt of thermoplastic polyurethaneurea and curing said polyurethaneurea with said atmospheric moisture.

22. The method of claim 21 wherein said combining step is performed with a polyglycol selected from the group consisting of a silicone glycol, a polyester lycol, polylactone lycol and a polyether glycol.

23. A method for producing a melt processable polyurethaneurea consisting essentially of adding 4,4'-diphenylmethane diisocyanate, with mixing, to a mixture of 1,4-butanediol, polytetramethylene ether glycol and an amine terminated polypropylene oxide at a temperature sufficient to induce an exotherm to give a clear uniform melt of a polyurethaneurea and moisture curing said polyurethaneurea.

* * * * *